US009480539B2

(12) United States Patent
Ortlieb

(10) Patent No.: US 9,480,539 B2
(45) Date of Patent: Nov. 1, 2016

(54) VIEWING SYSTEM AND VIEWING METHOD FOR ASSISTING USER IN CARRYING OUT SURGERY BY IDENTIFYING A TARGET IMAGE

(71) Applicant: James Ortlieb, Edmonton (CA)

(72) Inventor: James Ortlieb, Edmonton (CA)

(*) Notice: Subject to any disclaimer, the term of this patent is extended or adjusted under 35 U.S.C. 154(b) by 320 days.

(21) Appl. No.: 13/663,584

(22) Filed: Oct. 30, 2012

(65) Prior Publication Data
US 2013/0113900 A1 May 9, 2013

Related U.S. Application Data

(60) Provisional application No. 61/555,369, filed on Nov. 3, 2011.

(51) Int. Cl.
| H04N 13/04 | (2006.01) |
| A61C 3/00 | (2006.01) |
| H04N 7/18 | (2006.01) |
| A61B 1/247 | (2006.01) |

(52) U.S. Cl.
CPC ............ *A61C 3/00* (2013.01); *A61B 1/247* (2013.01); *G06K 2209/057* (2013.01); *H04N 7/18* (2013.01); *H04N 13/044* (2013.01); *H04N 13/0438* (2013.01); *H04N 13/0484* (2013.01)

(58) Field of Classification Search
CPC .... A61C 3/00; G06K 2209/057; G06K 9/46; H04N 13/0438; H04N 13/044; H04N 13/0484; H04N 7/18; H04N 13/04
See application file for complete search history.

(56) References Cited

U.S. PATENT DOCUMENTS

| 4,727,416 | A | | 2/1988 | Cooper | |
| 4,915,626 | A | | 4/1990 | Lemmey | |
| 4,994,910 | A | | 2/1991 | Williams | |
| 5,016,098 | A | | 5/1991 | Cooper | |
| 5,027,138 | A | | 6/1991 | Cooper | |
| 5,051,823 | A | | 9/1991 | Cooper | |
| 5,115,307 | A | * | 5/1992 | Cooper et al. .................. | 348/66 |
| 5,131,844 | A | | 7/1992 | Marinaccio | |
| 5,251,025 | A | | 10/1993 | Cooper | |
| 5,274,535 | A | | 12/1993 | Gonser | |
| 5,347,431 | A | | 9/1994 | Blackwell | |
| 5,634,790 | A | * | 6/1997 | Pathmanabhan et al. ...... | 433/29 |
| 5,745,165 | A | | 4/1998 | Atsuta | |
| 5,803,905 | A | | 9/1998 | Allred | |
| 5,808,680 | A | | 9/1998 | Steckhan | |
| 5,836,762 | A | | 11/1998 | Peithman | |
| 5,836,869 | A | | 11/1998 | Kudo | |
| 5,867,210 | A | | 2/1999 | Rod | |
| 6,086,228 | A | | 7/2000 | McGowan | |
| 6,368,332 | B1 | * | 4/2002 | Salcudean ............. | A61B 19/26 128/897 |
| 6,414,708 | B1 | | 7/2002 | Carmeli | |
| 6,561,972 | B2 | | 5/2003 | Ooshima | |
| 6,640,128 | B2 | | 10/2003 | Vilsmeier | |

(Continued)

*Primary Examiner* — Jay Patel
*Assistant Examiner* — Francis G Geroleo
(74) *Attorney, Agent, or Firm* — Buchanan Nipper LLC

(57) ABSTRACT

A viewing system includes a detector of electromagnetic radiation (EMR); and a control system connected to receive signals from the detector, and configured to identify an image locator, disposed within a field of view of the detector in use, and select for detection by the detector the image locator or an image located by the image locator. A viewing method includes detecting electromagnetic radiation from an image locator disposed within a field of view of a detector; identifying the image locator with a control system; and displaying the image locator or an image located by the image locator on one or more displays.

20 Claims, 6 Drawing Sheets

(56) References Cited

U.S. PATENT DOCUMENTS

| | | |
|---|---|---|
| 6,644,837 B2 | 11/2003 | Borders |
| 6,899,442 B2 | 5/2005 | Howell |
| 6,919,914 B2 | 7/2005 | Beutter |
| 7,305,180 B2 | 12/2007 | Labaziewicz |
| 7,321,385 B2 | 1/2008 | Rus |
| 7,362,966 B2 | 4/2008 | Uchiyama |
| 7,417,673 B2 | 8/2008 | Wright |
| 7,425,077 B2 | 9/2008 | Lockamy |
| 7,433,505 B2 | 10/2008 | Yoo |
| 7,443,417 B1 | 10/2008 | Heinrich |
| 7,509,041 B2 | 3/2009 | Hosono |
| 7,577,344 B2 | 8/2009 | Kakiuchi |
| 7,600,892 B2 | 10/2009 | Belliveau |
| 7,607,798 B2 | 10/2009 | Panotopoulos |
| 7,620,228 B2 | 11/2009 | Yoo |
| 7,699,506 B2 | 4/2010 | Andersen |
| 7,713,058 B2 | 5/2010 | Takahashi |
| 7,778,537 B2 | 8/2010 | Guan |
| 7,794,396 B2 | 9/2010 | Gattani |
| 7,801,431 B2 | 9/2010 | Wang |
| 7,841,731 B2 | 11/2010 | Marka |
| 7,860,289 B2 | 12/2010 | Yoo |
| 7,871,375 B2 | 1/2011 | Talieh |
| 2002/0086262 A1 | 7/2002 | Rainey |
| 2003/0185009 A1 | 10/2003 | Walters |
| 2005/0163342 A1* | 7/2005 | Persky .......................... 382/103 |
| 2005/0267335 A1 | 12/2005 | Matsui |
| 2006/0001740 A1 | 1/2006 | Fujie |
| 2006/0215406 A1 | 9/2006 | Thrailkill |
| 2006/0232665 A1* | 10/2006 | Schowengerdt et al. ....... 348/51 |
| 2007/0052803 A1* | 3/2007 | Chosak ............ G08B 13/19608 348/143 |
| 2007/0242447 A1 | 10/2007 | Scholz |
| 2007/0265495 A1* | 11/2007 | Vayser ................... A61B 1/045 600/109 |
| 2009/0220131 A1 | 9/2009 | Cinquin |
| 2010/0021108 A1 | 1/2010 | Kang |
| 2010/0112511 A1 | 5/2010 | Wu |
| 2010/0141739 A1* | 6/2010 | Luber et al. ..................... 348/46 |
| 2012/0019632 A1* | 1/2012 | Nakajima ........................ 348/51 |
| 2013/0131505 A1* | 5/2013 | Daon et al. ..................... 600/426 |
| 2014/0055563 A1* | 2/2014 | Jessop ............................. 348/45 |

\* cited by examiner

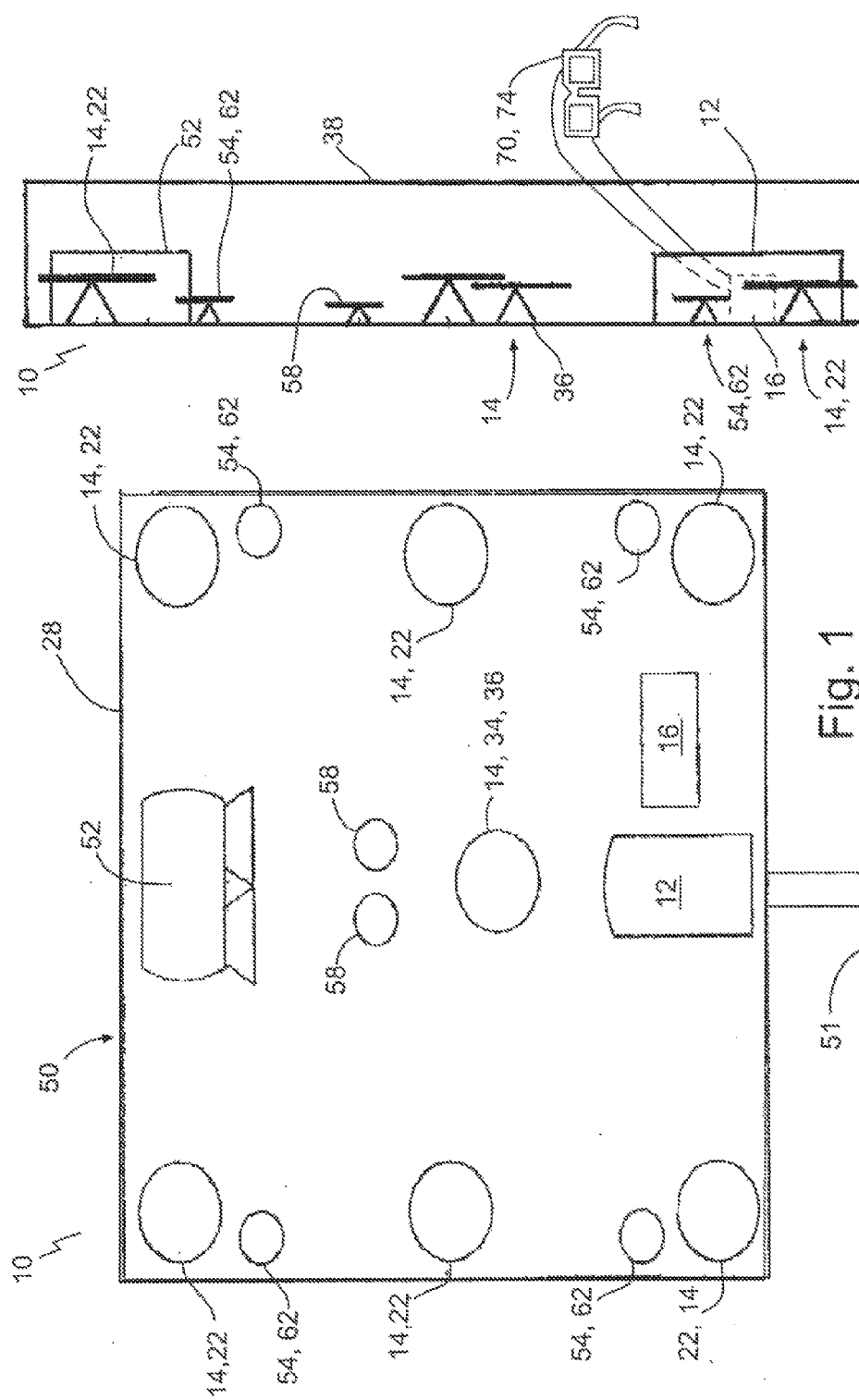

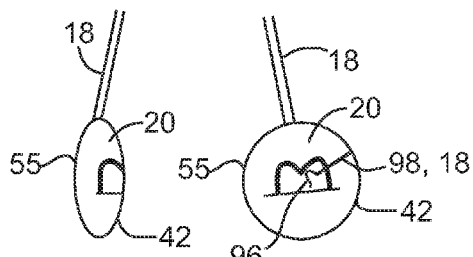
Fig. 3A
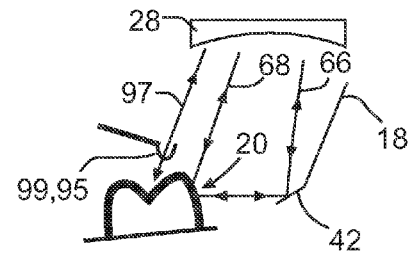
Fig. 3B
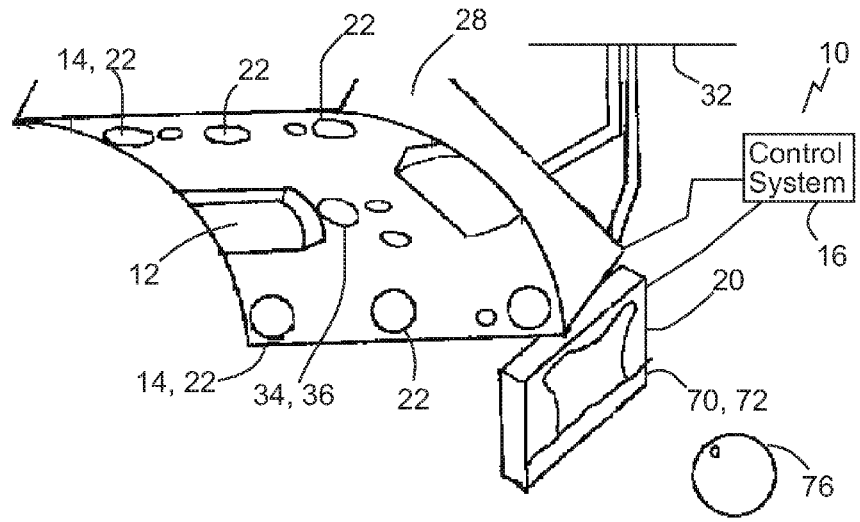
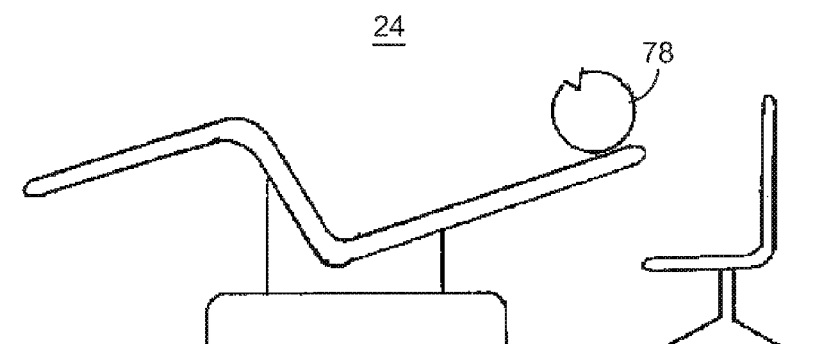
Fig. 4

VIEWING SYSTEM AND VIEWING METHOD FOR ASSISTING USER IN CARRYING OUT SURGERY BY IDENTIFYING A TARGET IMAGE

CROSS-REFERENCE TO RELATED APPLICATIONS

This application claims the benefit under 35 USC 119(e) of U.S. provisional application Ser. No. 61/555,369 filed Nov. 3, 2011.

TECHNICAL FIELD

This document relates to a viewing system and viewing method.

BACKGROUND

Video systems exist to assist a physician in carrying out surgery. Exemplary systems track a specialized tool and automatically modify the zoom level or displace a camera endoscope to maintain the tool in the field of view of the camera.

SUMMARY

A viewing system is disclosed, comprising: a detector of electromagnetic radiation (EMR); and a control system connected to receive signals from the detector, and configured to identify an image locator, disposed within a field of view of the detector in use, and select for detection by the detector an image located by the image locator.

A viewing method is disclosed comprising: detecting electromagnetic radiation from an image locator disposed within a field of view of a detector; identifying the image locator with a control system; and displaying an image located by the image locator on one or more displays.

A viewing system is also disclosed, comprising: a detector of electromagnetic radiation; plural receiver elements spaced laterally from one another relative to a target area in front of the receiver elements for directing electromagnetic radiation from an image locator, disposed within the target area in use, to the detector; and a control system connected to receive signals from the detector, and configured to identify the image locator and select for detection by the detector the image locator or an image located by the image locator.

A viewing method is also disclosed comprising: directing electromagnetic radiation, with plural receiver elements spaced laterally from one another relative to a target area in front of the receiver elements, from an image locator to a detector; identifying the image locator with a control system; and displaying the image locator or an image located by the image locator on one or more displays.

A viewing system is disclosed, comprising: a detector of electromagnetic radiation (EMR); an image locator; controllable optical elements for directing electromagnetic radiation from the image locator to the detector; and a control system connected to receive signals from the detector, identify the image locator and to select for detection by the detector an image defined by the image locator.

In various embodiments, there may be included any one or more of the following features: An illumination system comprising a one or more generators of electromagnetic radiation, in which the control system is connected to direct electromagnetic radiation from the one or more generators to a target. The target is identified by the image locator. The illumination system comprises one or more controllable electromagnetic radiation guides for directing electromagnetic radiation from the one or more generators. The image locator comprises a distinct image locating element. The distinct image locating element comprises an electromagnetic radiation guide. The distinct image locating element comprises a mirror. The distinct image locating element defines a passage for electromagnetic radiation. The image locator comprises a dental tool. The dental tool comprises a conventional dental tool. The image locator further comprises an anatomical feature. One or more controllable electromagnetic radiation guides for directing electromagnetic radiation from the image locator to the detector. The one or more controllable electromagnetic radiation guides for directing electromagnetic radiation from the image locator to the detector comprise plural receiver elements spaced laterally from one another relative to a target area in front of the receiver elements. The plural receiver elements are mounted on a frame. The frame is mounted on one or more of a wall, floor, or ceiling. The one or more controllable electromagnetic radiation guides for directing electromagnetic radiation from the image locator to the detector comprise one or more intermediate guides connected to direct electromagnetic radiation from one of more of the plural receiver elements to the detector. The one or more controllable electromagnetic radiation guides for directing electromagnetic radiation from the image locator to the detector comprise one or more fiber optic cables. The one or more controllable electromagnetic radiation guides for directing electromagnetic radiation from the image locator to the detector comprise one or more optical elements. One or more displays are connected to display the image or image locator. The one or more displays comprises a head mounted 3D display. The one or more displays are connected to co-display a first image of the image or image locator with a second image, and further comprising a patient selective filter for blocking electromagnetic radiation from the display of the first image and a user selective filter for blocking electromagnetic radiation from the display of the second image. The selective filter comprises one or more active or passive viewers. An eye tracker is connected to send control signals to the control system. The detector comprises two or more detectors. The control system is configured to identify a second image locator, disposed within the image located by the image locator in use, and select for detection by the detector the second image locator or a second image located by the second image locator. Detecting further comprises directing electromagnetic radiation with one or more controllable electromagnetic radiation guides from the image locator to the detector. Identifying the image locator comprises cycling through plural fields of view received by one or more controllable electromagnetic radiation guides until the image locator is identified. The image locator is identifiable within two or more fields of view of plural fields of view received by the one or more controllable electromagnetic radiation guides, and further comprising selecting one or more of the two or more fields of view for display based on predetermined criteria. The image locator comprises a distinct image locating element, the predetermined criteria comprises a desired shape, and selecting one or more of the two or more fields of view further comprises selecting a field of view that includes a shape, of the distinct image locating element, that most closely corresponds to the desired shape. The image is located directly or indirectly by the image locator. Two or more image locators are disposed within the field of view of the detector, and in which the image locator that locates the image displayed on the one or more displays is selected on the basis of one or more predetermined criteria.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which:

FIG. 1 is a front elevation view of a viewing system.

FIG. 2 is a side elevation view of the viewing system of FIG. 1

FIG. 3A illustrates an image reflected in a dental mirror as viewed from differently spaced receptor elements of the controllable optical elements.

FIG. 3B is a side elevation view of tooth, hooked shaped tool, and dental mirror.

FIG. 4 is a perspective view of the viewing system of FIG. 1 with a display and mounted to a ceiling to view a fully reclined patient.

DETAILED DESCRIPTION

Figure 3:
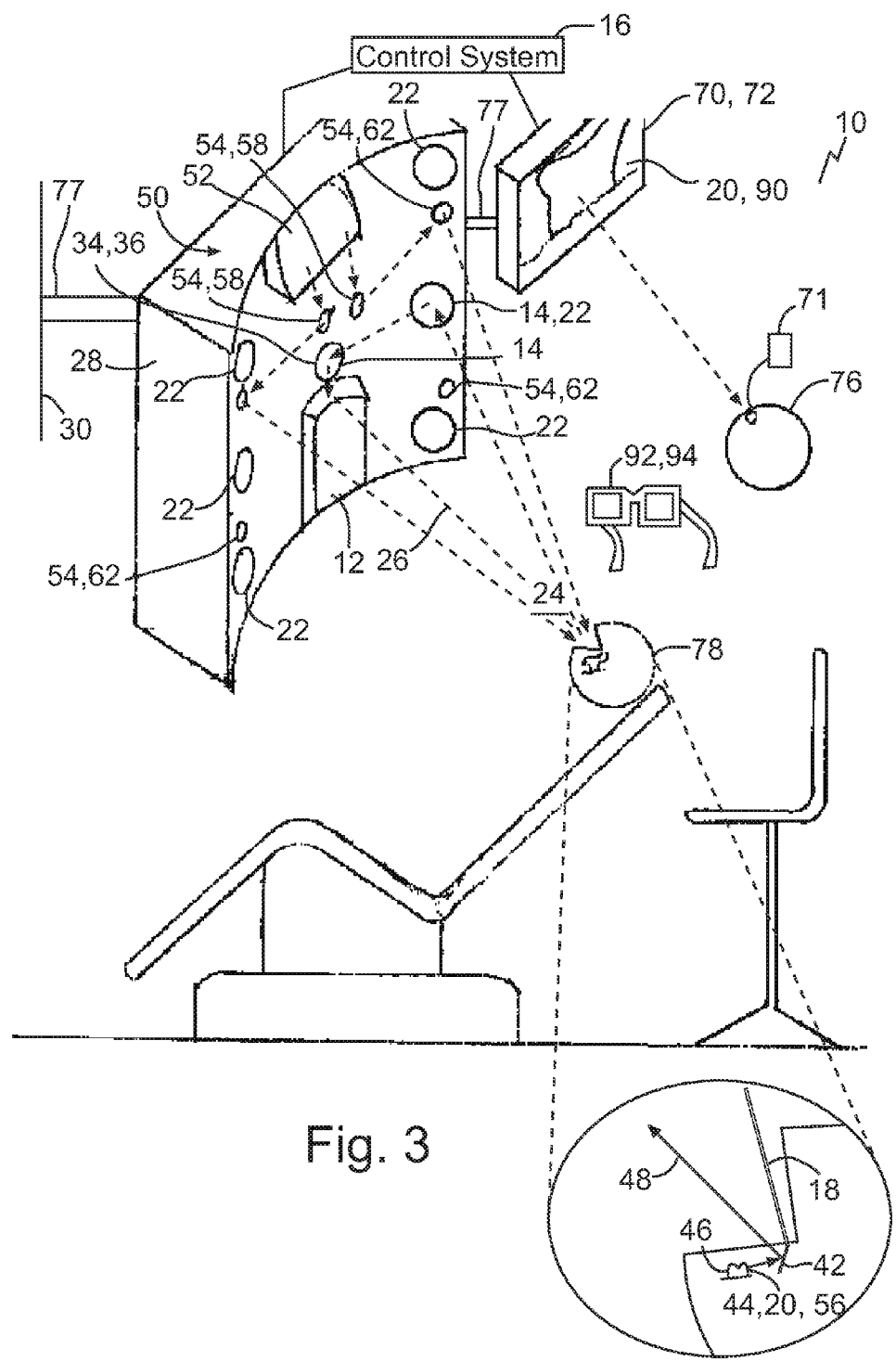
FIG. 3 is a perspective view of the viewing system of FIG. 1 with a display and mounted on a wall to view a partially reclined patient.

Immaterial modifications may be made to the embodiments described here without departing from what is covered by the claims.

Dentists and medical doctors routinely perform surgery in a poorly lit body cavity. Age and other factors may affect the ability of the eye to focus at closer distances and the lens of the eye may lose flexibility with age. The lens may also be unable to accommodate and produce clear images of closer objects. Thus, in some cases a person may only be able to discern a small feature by moving the eyes further from the feature until clarity is resolved. This method of focusing makes objects smaller and more difficult to see. Corrective glasses may be used to adjust the visual focal length and improve visual acuity, however there may still be a tendency for practitioners to bend over and get closer to an object to increase its size, which may lead to poor posture and job stress.

In addition, many body cavities may be difficult for the physician to reach without assuming an awkward body posture. The physician's need to see into patient's body may result in hyper extension of the spinal, muscle and ligature tissues, among other injuries. The cost of such injuries to the physician and society may be considerable.

Referring to FIGS. 1-4, a viewing system 10 and viewing method is illustrated, the viewing system 10 comprising a detector 12, and a control system 16. Detector 12 detects electromagnetic radiation (EMR), such as visible light, invisible light, or other suitable wavelengths of EMR. Control system 16 is connected to receive signals from the detector 12, and is configured to identify an image locator 18, disposed within a field of view of the detector in use, and select for detection by the detector 12 the image locator 18 or an image 20 (FIG. 3A) located by the image locator 18.

System 10 may include one or more controllable electromagnetic radiation guides 14, which direct electromagnetic radiation from an image locator 18 to the detector 12. The viewing method may be carried out by detecting EMR, for example directed with one or more controllable electromagnetic radiation guides 14, from image locator 18 to detector 12, and identifying image locator 18 with control system 16. The image locator 18 or an image 20 located by the image locator 18 may then be displayed on one or more displays.

Referring to FIGS. 1, 2, 3, and 4, the controllable electromagnetic radiation guides 14, for example optical elements, may comprise plural receiver elements 22 spaced laterally from one another relative to a target area 24 (FIG. 3) in front of the receiver elements 22. For example as shown, the plural receiver elements 22 are mounted on a frame 28, which may be mounted on one or more of a wall 30 (FIG. 3) or ceiling 32 (FIG. 4). Frame 28 may also be mounted on a floor 51 (FIG. 1) in some cases. Lateral spacing is understood to mean relative spacing from the perspective of a viewer looking down a theoretical axis 26 (FIG. 3) defined from the viewing system 10 to the target area 24, and is not restricted to horizontal spacing, vertical spacing, or spacing within a plane perpendicular to axis 26. Spacing receiver elements 22 laterally in the context of this document allows each receiver element 22 to be capable of receiving a field of view or set of fields of view of the target area 24 distinct from the fields of view of the other receiver elements 22. Thus, by manipulation of the controllable electromagnetic radiation guides 14, detector 12 may view one or more different fields of view as desired. Such flexibility is advantageous for example in the context of surgery within a tight cavity such as a patient's mouth, where use of different angles may be required to discern the various features of interest within the cavity. The frame 28 may comprise a cover 38 (FIG. 2), such as a glass cover, that is transparent to the EMR used by the system 10. Frame 28 may have a suitable shape, such as a planar or curved (as shown) working surface.

The controllable electromagnetic radiation guides 14 may further comprise one or more intermediate guides 34, such as a primary mirror 36 as shown, connected to direct electromagnetic radiation from one or more of the plural receiver elements 22 to the detector 12. Other elements 14 not shown may intercept or redirect electromagnetic radiation to facilitate travel from a receiver element 22 to the guide 34. More than one guide element 34 may be used.

The controllable electromagnetic radiation guides 14 may comprise one or more of lenses, mirrors, magnets, prisms, beam splitters, reflective and refractive surfaces and other materials suitable to guide waveforms of visible and invisible electromagnetic radiation from the target area 24 to the detector 12. Controllable electromagnetic radiation guides 14 include one or more adjustable elements, which may be controlled using robotics, motors, such as electromagnetic, solid state (piezo), or mechanical actuators, gimbals, or magnetic field generators. Other suitable control mechanisms may be used. Each controllable electromagnetic radiation guide 14 may be capable of rotating about one or more axes, lateral panning, lateral trolleying, or displacement towards or away from target area 24. Other suitable movements may be used.

Referring to FIGS. 3, 3A, and 3B, in some embodiments the control system 16 selects for detection an image 20 located by the image locator 18. Thus, the system 16 effectively tracks an image 20 whose features are defined external to the image locator 18 but which is located, or otherwise pointed to, by the locator 18. For such a purpose the image locator 18 may comprise a distinct image locating element, for example an electromagnetic radiation guide such as a mirror (illustrated by dental mirror 42). The image locator 18 may comprise a dental tool, such as conventional dental mirror 42 as shown. Thus, for example as shown in FIG. 3, the image locator 18 may use mirror 42 to locate an image 20 of a side 44, of a tooth 46, that faces away from frame or box 28. Once image locator 18 is detected, control system 16 instructs electromagnetic radiation guides 14 to select image 20 for detection by detector 12, by directing EMR 48 from image 20 to detector 12. Other examples of suitable distinct image locating elements include an element that defines a passage 99 (FIG. 3B) for EMR 97 to pass through. A suitable passage 99 includes for example a hook 95 as shown, a cylinder, a closed loop, or other suitable shapes. Selecting for detection includes manipulating the controllable electromagnetic radiation guides 14, for example to focus on image 20, to increase or decrease magnification of image 20, or to view image 20 from a different field of view. The dental tool may be a conventional dental tool, which the control system 16 may automatically track upon entry of the tool within the target area 24.

Referring to FIG. 3B, although the image 20 may be tracked indirectly by the control system 16 using image locator 18 (EMR path 66), the image 20 may also be tracked directly (EMR path 68). Thus, the image 20 may be located directly or indirectly by the image locator 18. In a direct tracking embodiment control system 16 effectively locates the image 20 using image locator 18, and then selects the image 20 for direct viewing if a direct line of sight exists between the image 20 and a receiver element 22. In effect the image locator 18 points to a feature, such as an anatomical feature (ex. tooth 46), within the mouth of the patient 78, and the system 16 tracks that feature.

In some cases, control system 16 may track the image locator 18 itself, for example if the tip 96 of a scraper 98 (FIG. 3A) is tracked. In some cases, a further image locator 18 such as scraper 98 is tracked by first identifying image 20 with image locator 18, identifying scraper 98 within image 20, and selecting scraper 98 for detection by the detector 12. In an example, if scraper 98 moves outside of image 20 or outside a predetermined perimeter defined within image 20, control system 16 cycles through different fields of view using controllable electromagnetic radiation guides 14 to find a suitable view of scraper 98 within image 20 located by image locator 18. In another example such an occurrence could trigger a priority switch between scraper 98 and image locator 18, so that control system 16 looks for scraper 98 directly. In general, in some cases if image locator 18 moves outside of the field of view of a receiver element or outside a predetermined perimeter defined within the same field of view, control system 16 cycles through different fields of view using controllable electromagnetic radiation guides 14 to find a suitable view of image locator 18, for example mirror 42 or scraper 98.

While the foregoing may describe a method of selecting a suitable image 20 when the image locator 18 is identifiable within two or more fields of view, other view selection methods may be used. In general, selecting one or more of the two or more fields of view for display may be based on predetermined criteria. For example in FIG. 3A, the predetermined criteria comprises a desired shape, such as a circle or ellipse of predetermined eccentricity, and selecting one or more of the two or more fields of view further comprises selecting a field of view that includes a shape 55, of the distinct image locating element (mirror 42), that most closely corresponds to the desired shape. Thus, if the desired shape is a perfect circle, then control system 16 selects the view, in this case the right most view, of mirror 42 that most closely corresponds with a perfect circle. Other view selection methods may be used, and may be overridden by manual control.

In some cases, the image locator 18 may not be present in the immediate field of view being tracked, or may have moved outside of a predetermined perimeter defined in the field of view being tracked. In such a case, system 16 may cycle through plural fields of view received by the controllable electromagnetic radiation guides 14 until the image locator 18 is identified. If not located, the system 16 may wait for the image locator 18 to appear, or may repeat one or more cycles in search of the locator 18. In some cases, the system 16 begins tracking image locator 18 only when image locator 18 is moved into the line of sight of a field of view received by a designated or suitable receiver element 22. Thus, to wake up the system 16, a user 76 may move the image locator 18 into the target area 24 and begin work on patient 78.

Referring to FIGS. 1, 2, and 3, the viewing system 10 may comprise an illumination system 50 having a generator 52 of EMR. Illumination system 50 may also have a second set of one or more controllable electromagnetic radiation guides 54 for directing EMR from the generator 52. Generator 52 may be a source of one or more of visible and invisible electromagnetic radiation, and may produce more than one wavelength, range of wavelengths, or distinct streams of EMR at a time. The control system 16 may be further connected to direct EMR to a target 56, for example identified by the image locator 18. The controllable electromagnetic radiation guides 50 may further comprise one or more guide elements 58, such as primary mirrors as shown, connected to direct electromagnetic radiation from the generator 52 to one or more plural transmitter elements 62 spaced laterally from one another relative to a target area 24 in front of the transmitter elements 62. Other elements 50 not shown may intercept or redirect EMR to facilitate EMR travel from generator 52 to transmitter elements 62. In one embodiment there are two or more guide elements 58 to ensure that there is always two or more distinct paths of EMR oriented towards target 56 for example to dispel shadows. In some cases each transmitter element 62 may have a corresponding generator 52 or supply of EMR from generator 52 for simultaneous transmission of EMR from one, two, or all elements 62. In some embodiments control system 16 detects shadows and targets EMR to eliminate or reduce such shadows. Referring to FIG. 3B, the target 56 may be the image 20, for example if the system 16 directs EMR directly onto the image 20 (EMR path 68) or indirectly through the distinct image locating element (EMR path 66). In other embodiments the target 56 is part of the image locator 18 itself, or another suitable target 56.

Similar to controllable electromagnetic radiation guides 14, the illumination system 50 may comprises one or more of lenses, mirrors, magnets, prisms, beam splitters, reflective and refractive surfaces and other materials suitable to guide waveforms of visible and invisible electromagnetic radiation from the radiation generator(s) 52 to the patient 78. System 50 include one or more adjustable elements, which may be controlled using robotics, motors, such as electromagnetic, solid state (piezo), and mechanical actuators, gimbals, or magnetic field generators. Other suitable control mechanisms may be used. Each controllable electromagnetic radiation guide 50 may be capable of rotating about one or more axes, lateral panning, lateral trolleying, or displacement towards or away from target area 24. Other suitable movements may be used.

Radiation generators can include incandescent, fluorescent, arc, and LED light sources, and sources of invisible radiation. Radiation can be further manipulated by filters, prisms, magnets, reflective and refractive surfaces to alter the characteristics of the radiation. In some cases the radiation generated could be selected to cause fluorescence of compounds present in the target area 24, for example after ingestion or topical application of such compounds.

Referring to FIGS. 2, 3 and 4, viewing system 10 may comprise a display 70 connected, for example to control system 16, to display the image 20 or image locator 18. Display 70 may be a suitable display, such as a monitor 72 (FIGS. 3 and 4), or a head mounted display such as a pair of head mounted 3D viewers (glasses 74—FIG. 2). For 3D glasses 74, at least two detectors 12 may be used in order to display distinct fields of view, which may be laterally spaced to correspond with the eye to eye spacing of a user 76. In other cases, 2D viewers (not shown) may be used. Plural distinct images may be simultaneously displayed on display 70, which may be more than one display 70, for example using a picture in picture mode (not shown). Display 70 allows user 76 to view target area 24, for example image 20, of patient 78 in real-time, in order to allow user 76 to carry out surgery without having to bend or strain in awkward positions required to directly view the surgery as may otherwise be necessary.

Referring to FIG. 3, the display 70 may be connected to co-display a first image 90 of the image 20 or image locator 18 with a second image (not shown), which may be an image from a television program or other media suitable for viewing by patient 78 who is awake during the procedure. The first and second images may be layered together. A selective filter 92, for example in the form of filter viewers such as glasses 94, may be provided for blocking EMR from the display 70 of the first image 90. The selective filter 92 may comprise one or more active or passive viewers. Thus, the same display 70 may be used to simultaneously display the two images, allowing the patient 78 to view the second image and the user 76 to view the first image 90. User 76 may require a selective filter (not shown) for blocking EMR from the display 70 of the second image. One or both of the patient or user selective filters may include a hood, visor, screen shield, interlace eyewear, polarized glasses, shutter glasses, and other suitable active or passive filters. In some cases, the display 70 may be entirely blocked from the patient's view. A similar method of image layering and filtering may be used to allow two or more video game players or television viewers to watch the same display device and yet each see a completely different scene (FIG. 7 and corresponding description paragraphs). Also one or more users may see the same scene when filters are synchronized.

Display 70 may display one or more of a direct feed from detector 12, or a mirror image of the feed. In some cases display 70 displays a rotated image of the feed, for example to give user 76 a user friendly perspective. For example, control system 16 may be calibrated to always display an image of a row of teeth in a horizontal orientation, with the top of the teeth pointing vertically up or down. Display parameters may be set by user preferences.

Figure 5:
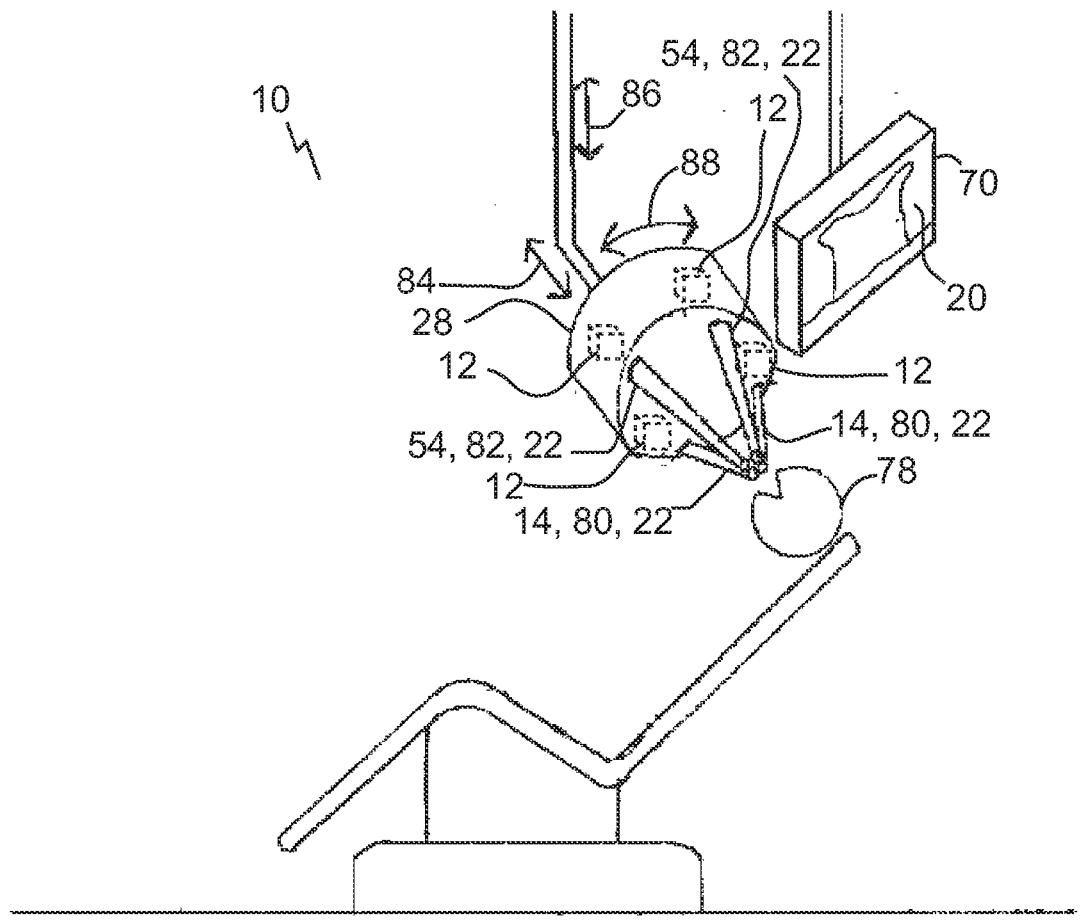
FIG. 5 is a perspective view of another embodiment of a viewing system with a display.

Referring to FIG. 5, another embodiment of viewing system 10 is illustrated, in which the controllable electromagnetic radiation guides 14 comprise one or more fiber optic cables 80. Controllable electromagnetic radiation guides 54 may also comprise one or more fiber optic cables 82. Each Cable 80 may be connected to selectively direct EMR to a single or plural detectors 12. It may be advantageous to use plural detectors 12, for example one or more detectors 12 for each receiver element 22, to allow continuous monitoring of two or more or all fields of view at once, and to allow quicker switching or cycling between fields of view. As shown in FIG. 5, electromagnetic radiation guides 14 may be movable, for example laterally displaceable along direction lines 86 and 88, for further example by laterally displacing frame 28 as shown. Axial displacement, for example along the direction lines 84, may also be used for electromagnetic radiation guides 14 or frame 28. In some cases, frame 28 or electromagnetic radiation guides 14 are repositionable along or about two or more axes of motion, for example perpendicular axes of motion. Lenses (not shown) may be provided at the ends of fibre optic cables 80, 82, although such an arrangement may offer reduced options for focal length change, hence the use of a robotic head (Frame 28) that can physically rotate and move in/out and up/down or by other suitable movements. Each element 14 may function as an element 54, and vice versa to add functionality.

The image locator 18 may be a conventional tool used in surgery, such as a scalpel (not shown), dental mirror 42, scraper 98, floss, drill, or other tools. The image locator 18 may also be an anatomical feature, such as a tooth 46, material or tissue on the image locator 18, or a user's 76 finger (not shown). In the latter example a user 76, such as a dental assistant, may point to a feature within a patient 78 in order for the system 16 to track that feature. When floss is used as image locator 18, the image 20 tracked by system 16 may include a suitable feature such as the intersection between the teeth where the floss is inserted, or the adjacent teeth. The image locator 18 may be any shape trained into memory. One or more image locators 18 may be tracked at a given time. In some cases, the system 16 may have a predetermined criteria such as a priority list of locators 18 to track, for example 1—dental mirror, 2—scraper, 3—finger, 4—patient's mouth. The priority list may work to instruct control system 16 which type of image locator 18 to look for first, and if the first type is not found, the system 16 then looks for the next type of image locator 18, and so on. In other cases the priority list works to instruct the control system 16 which image locator 18 to find first, and upon finding the first type the control system 16 then looks for the next type of image locator 18 within the image 20 located by the image locator 18, failing which, the next type is checked within image 20, and so on.

Referring to FIG. 3, a viewing system 10 may comprise controllable electromagnetic radiation guides 14, detector 12, display 70 and an eye tracker 71 such as a retinal scanner, connected to send control signals to the control system 16. Thus, the eye activity of user 76 viewing display 70 may be used to control the system 16. Such a methodology is advantageous because it allows a user 76 to provide manual instructions to the system 16 with eye movements, which may give quicker response than other physical instruction methods such as arm or leg movement, or vocal commands. For example, a user 76 may wish to view a feature outside the immediate field of view displayed on display 70, so user 76 may carry out a particular eye movement predetermined to change the displayed view as desired, for example by moving a focal point of the user's 76 eye to the left side of display 70 in order to pan left. In other cases a user 76 may use the user's eye to select features and controls from a menu on display 70. Other predetermined commands may be used to carry out functions such as zooming in and out, panning, switching angles, and other useful commands. Some movements may be passive, for example if the system 16 is calibrated to zoom into an area the user 76 has been staring at for a predetermined amount of time.

A pedal board (not shown) or other manual input device may be used in conjunction to provide a variety of manual control options. A user 76 may use manual inputs to override the automation of the system 16 in some cases, for example by switching into a manual mode. Other manual input devices, also referred to as pointing devices, may include keyboards, touch screens, voice commands, laser pointers, mouse peripherals, joysticks, foot pedals, retinal sensors, and other suitable devices suitable to guide the detector's gaze.

Identification of the image locator 18 may be done using one or more shape analysis algorithms. In some cases control system 16 may compute the optimal angle of view for display by understanding the known geometry of patient features, and image locators. In some cases the system 10 is configured to watch a user 76 and build a set of user preferences from observation, in order to tailor the system 10 to each particular user 76.

One or both display 70 and frame 28 may be mounted on one or more articulating arms 77 (FIG. 3). In some cases a floor stand 51 may be used to mount one or more components of system 10.

Although the viewing system 10 and method are described above mainly for use in surgery applications, the viewing system 10 and method may be used in other suitable applications, for example in manufacturing or machining. In general, system 10 may be used advantageously in applications where it is difficult, awkward, or impossible to directly view a working feature, or where small details must be resolved and discerned.

The system 10 may be designed to recognize and track new tools, such as conventional tools. Image locator 18 need not have special markings for the system 16 to track locator 18. Priorities may be set by user preference.

The image locator 18 may be a laser point generated from a user's 76 laser pointer (not shown).

The image tracked by the image locator 18 may be an image that is pointed to by the image locator 18. For example, a scraper 98 may be used to point to a feature of interest, which is then tracked by the system 16.

Although display 70 is mentioned for real time viewing of the target area 24, in some cases the control system 16 is connected to store the image feed.

All EMR guides, including those in illumination system 50, may be receiver elements, transmitter elements or intermediate guides.

The field of view of a detector 12 or generator 52 may be modified by rotating, moving, tilting, panning, or other suitable movements.

Various routines carried out by one or more control systems 16 include: a) Recognize the shape of body parts, medical instruments and new pointing instruments (image locators) to guide the camera's gaze, b) Permit physicians to train the system to recognize new shapes. c) Determine the most desirable angle of view into the patient by internal shape analysis algorithms, artificial intelligence and/or input from the physician by pointing devices (manual input devices), and pointing instruments (image locators), c) Control the imaging and illumination mechanisms to obtain optimal images, d) Interpret and display images received from visible and non visible electromagnetic radiation waveforms.

Figure 6:
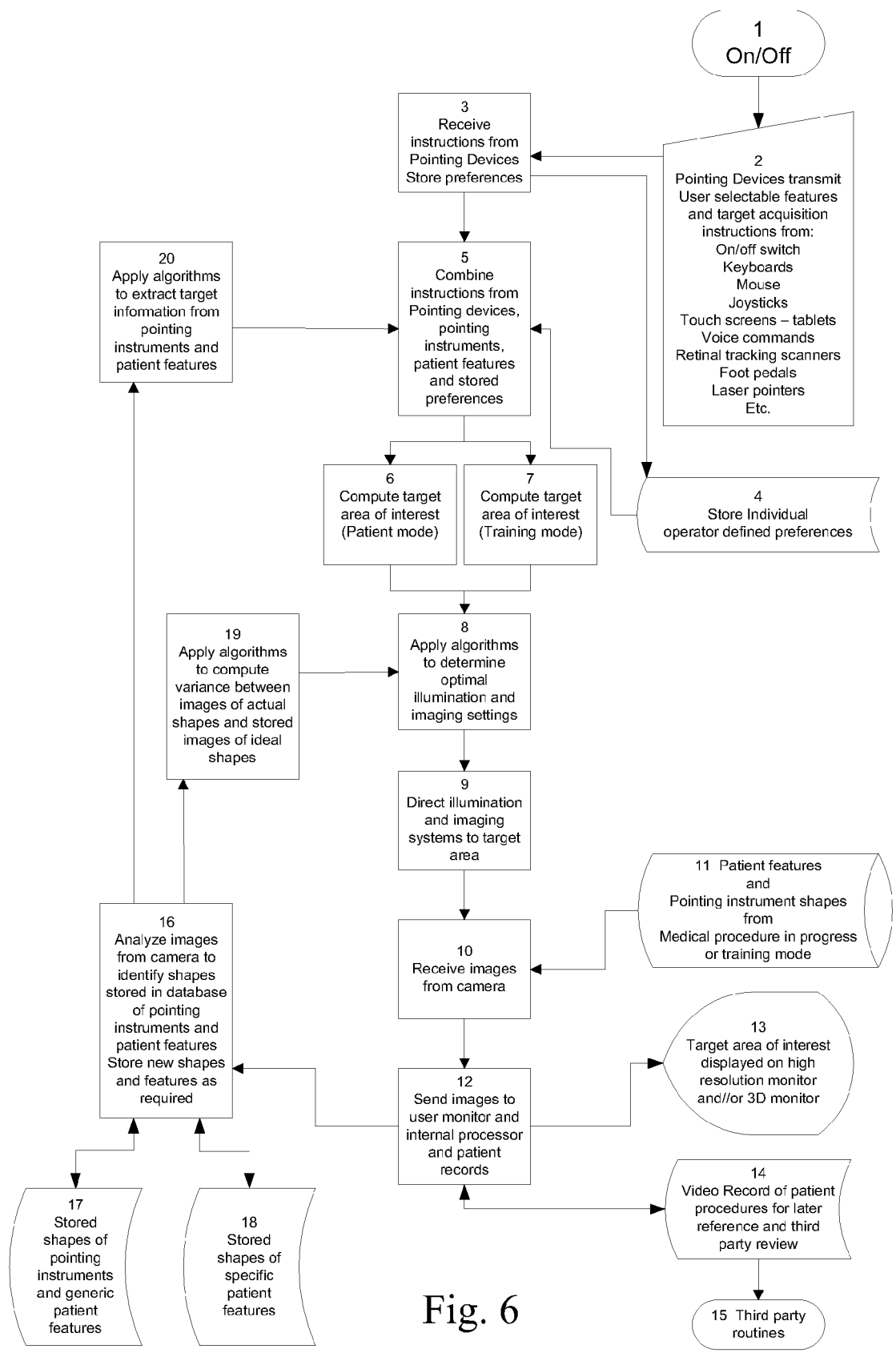
FIG. 6 is a flowchart of an example process control methodology for operating an embodiment of the apparatus.

Referring to FIG. 6, an exemplary process control diagram is illustrated. Item numbers in FIG. 6 are as follows:

1. A plug, switch, remote control or other device which sends a signal to either activate or deactivate the system.

2. Pointing devices are any peripheral devices in addition to those in item 1 that can be used to provide inputs to the system. The devices can include any of the hardware items listed in item 2, in addition to others. The purpose of these pointing devices is to: a) Manually direct the illumination and imaging systems of the viewing system 10 onto a target area, b) Select features from a menu of user customizable options such as: i) Lighting levels, brightness, contrast, color, hue, zoom, fade rates, view angles, shadow control, focus ii) Record or playback patient specific images iii) Operate in different electromagnetic wavelengths, iv) Select 2D or 3D imaging modes, v) Operate in real image or mirror image modes, vi) Send images to Dental Assistant monitor, vii) Set priority and override protocols between automatic and manual control inputs, viii) Set priorities for pointing instruments (image locators), and ix) Select from various language, time zone and other set up features, c) for any of the items in b, allow each operator to create their own profile of customized options (user preferences) which is stored and retrieved as users log on to the system, d) Download or transmit data from the viewing system 10 to external devices or recording media, patient record systems or third party systems, and e) Interlace or layer television programming onto display 70 for the patient to view, f) Direct the viewing system 10 to learn new pointing instrument (image locator) shapes by entering training mode.

3. The viewing system 10's processor (control system 16) receives instructions from pointing devices and stores user preferences as required.

4. Non volatile memory stores and retrieves user preferences and set up features.

5. The viewing system 10's processor combines inputs from pointing devices, pointing instruments, generic patient features, specific patient features and stored user preferences in order to compute target areas of interest. Items 5 through 20 form a continuous loop of the viewing system 10's control until operations are interrupted or suspended by inputs from pointing devices.

6. Patient mode will require the viewing system 10 to compute an ever changing target area of interest. Algorithms will process the target values of images of pointing instruments, generic patient features and specific patient features, and assess the priority structure of pointing devices, user behavior, and user preferences in order to identify the target area of interest. The target area is generally defined as a specific shape within some geographical location in the patient.

7. Training mode will require the viewing system 10 to learn new shapes of pointing instruments, generic patient shapes and specific patient shapes. Although the target area may be constant, a multitude of images are required to determine shape identification and ideal image definition of an object for later recognition. Generally the target area is defined as a geographical location in which the target shape is located.

8. Once the target has been identified and the variance between current images and ideal images has been determined, and the priority structure of pointing devices and user preferences has been incorporated, computations determine optimal illumination and imaging settings. Adjustments are made to illumination to provide ample lighting levels in the desired wavelength, and to reduce shadows. Adjustments are made to imaging to provide the best viewing angle, brightness, contrast, color, hue, zoom, focus, etc.

9. Algorithms convert the computation in item 8 into geometric instructions in order to control the various servos, motors, transducers, transistors, amplifiers, lamps and the like. Thus the illumination and imaging systems are physically manipulated.

10. The result is that the viewing system 10 receives images from its cameras.

11. Images are of patient features and pointing instruments found in the target area field of vision in either patient mode or training mode.

12. Patient mode and training mode Images are routed to physician and assistant display monitors (both 2D and 3D). Patient mode images are sent to non volatile memory for later reference or third party review. Both patient mode and training mode images are forwarded to the viewing system 10's processor for feedback into the control process.

13. Live or previously recorded images are displayed on high resolution monitors in 2D or 3D for physicians, dental assistants and patients to view.

14. Non volatile memory records live streaming images of the procedure when requested to do so by pointing devices. Audio may also be recorded.

15. Download or transmit data from the viewing system 10 to external devices or recording media, patient record systems or third party systems when requested to do so by pointing devices.

16. Images are analyzed. In patient mode images are compared to databases of pointing instruments, generic patient features and patient specific features to discover all recognizable shapes in the field of view. In training mode satisfactory images are stored in the appropriate database to facilitate shape identification and ideal image definition in the future.

17. Non volatile memory stores the shapes of pointing instruments and generic patient features in training mode. In patient mode images are retrieved for comparison to images received from the cameras.

18. Non volatile memory stores the shapes of specific patient features in training mode. In patient mode images are retrieved for comparison to images received from the cameras.

19. Algorithms are applied to the shapes identified in camera images to compute the variance between actual images and ideal images of various shapes. The variance is communicated to item 8 for feedback to assist in determining the adjustments required to improve illumination and imaging settings.

20. In patient mode algorithms are applied to the shapes identified in camera images to compute target values for each shape found. Target values are influenced by the number of shapes, the relative position of shapes, the types of shapes, and other criteria. The shapes of pointing instruments, generic patient features and specific patient features that are considered likely target areas of interest are passed along to item 5 for feedback into the viewing system 10's control process.

Multi-Viewer Embodiment

Presently, some display units such as televisions, monitors, projectors, headmounted 3D viewers and similar display units are capable of simultaneously layering, interlacing, or overlaying more than one image for presentation to the user. To the naked human eye the resulting layered picture appears fuzzy or distorted. The images that are layered together typically present a left and right eye perspective of a single scene for the purpose of offering the user a 3D experience. With the use of passive filters (polarized glasses) or active filters (e.g. shutter glasses) the left eye image is only visible to the left eye and the right eye image is only visible to the right eye thereby providing a 3D experience. Although several persons may watch the picture simultaneously, all users experience the same scene from the same program source at any given time.

Figure 7:
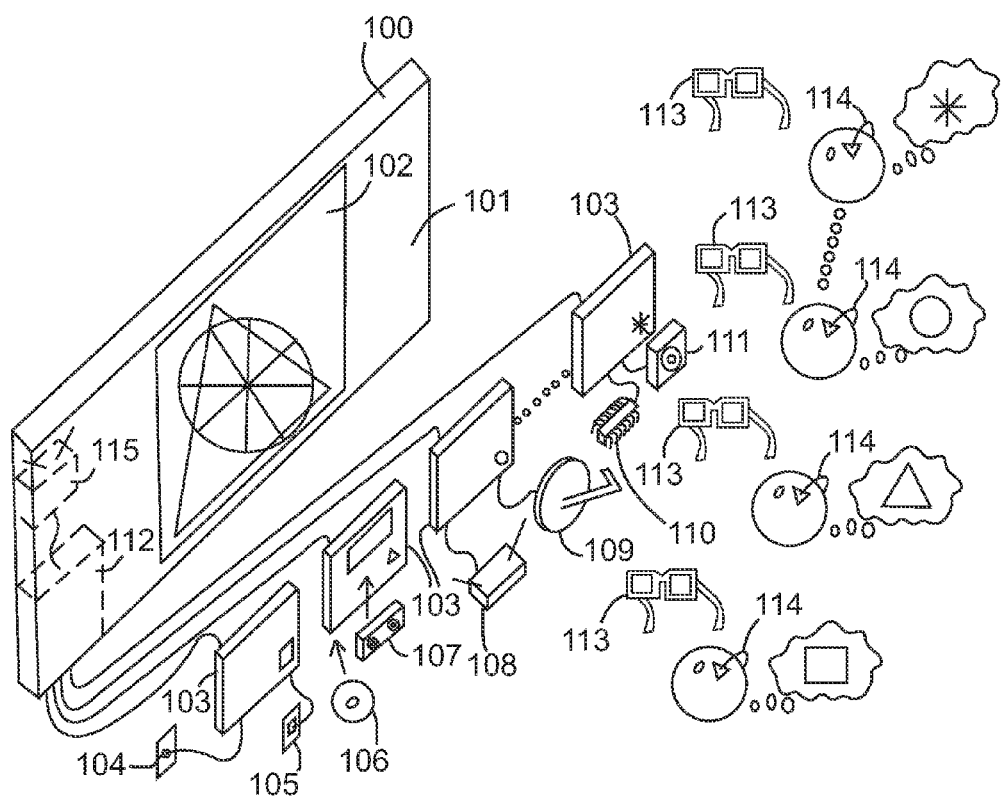
FIG. 7 is a perspective view of an example of a multi-viewer display embodiment.

The new embodiment disclosed in FIG. 7 allows one or more users to simultaneously watch a layered, interlaced or overlayed image, generated with content from one or more program sources, while each user is allowed to experience a unique or different scene along with the corresponding audio. Scenes may continue to be offered to one or more users in any combination of 2D or 3D perspective. Through individual headsets, the audio experience may also be synchronized to the passive or active filters to provide the corresponding sound channel to each user. Lastly, when passive or active filters are synchronized, one or more user may share the same experience while other users continue to have unique or different experiences.

The new embodiment offers several benefits. Money can be saved with the purchase of one display unit (e.g. a large screen television) that allows one or more users to each experience their own program source as though each person had their own display unit. Program sources can provide any combination of content such as live television programs, prerecorded programs, photos, home movies, video games, internet content, computer content or other content in any combination of 2D or 3D perspective. Video game enthusiasts can each enjoy a full size screen view of fields of play instead of much smaller halved, quartered or similarly fractioned split screens. A reduction in the number of display units also reduces the amount of space required and energy consumed.

Referring to FIG. 7, the display unit 100 may be a television, computer monitor, projector, headmounted 3D viewer or other type of equipment that produces an image on a display screen 101.

Images 102 may come from one or more program sources.

Program sources may come from one or more program devices 103 which send audio and video signals to the control unit. Program sources may provide analog or digital signals. Program devices may include analog or digital cable boxes, VCR players DVD players, game consoles, radio frequency tuners, satellite receivers, computers or other equipment that can send audio and video signals. Content for program devices may come from cable 104, the internet 105, DVD's 106, magnetic storage devices such as tapes 107, antennae 108, satellites dishes 109, memory chips 110, hard drives 111, or other media. Content may include live television programs, prerecorded programs, photos, home movies, video games, internet content, computer content or other content in any combination of 2D or 3D perspective.

The control unit 112 coordinates the audio and video signals from one or more program sources with each user that desires to experience that source. The control unit layers, interlaces or overlays video images onto the display screen. The control unit sends signals to the transmitter to synchronize passive or active filters 113 and audio headsets 114 to individual layers of video images. The control unit may also synchronize signals so that one or more user experiences the same program source while other users continue to have unique or different experiences. For one or more program sources the control unit may also send left and right eye video images to the display screen and corresponding signals to the transmitter to provide a 3D experience for one or more users.

The transmitter 115 receives signals from the control unit and sends them to the active filters and audio headsets of one or more users, for example through wired or wireless connections such as dedicated radio channels for each headset.

Passive or active filters are synchronized by the control unit through the transmitter to provide one or more users with a 2D or 3D video experience for the program source of their choice.

Audio headsets are synchronized by the control unit through the transmitter to provide one or more users with the sound information related to their 2D or 3D video experience.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A viewing system, comprising:
    a detector of electromagnetic radiation mounted on a frame;
    one or more controllable electromagnetic radiation guides mounted on the frame to guide electromagnetic radiation from a target area to the detector; and
    a control system connected to receive signals from the detector, and configured to:
        identify a dental mirror, disposed within a field of view of the detector in use,
        identify a feature of interest that is within the field of view and that is visible in the dental mirror,
        select for detection and tracking by the detector the feature of interest that is visible in the dental mirror by directing electromagnetic radiation to the detector using the dental mirror and the controllable electromagnetic radiation guides,
        track the dental mirror, and
        continue to track the feature of interest independently of the dental mirror, the feature of interest being distinct from the dental mirror;
        wherein the detection and tracking Includes manipulating the controllable electromagnetic radiation guides to view the feature of interest from a different field of view or optimal angle of view;
    displaying an image on a display in which the feature of interest is visible.

2. The viewing system of claim 1 further comprising an illumination system comprising one or more generators of electromagnetic radiation, in which the control system is connected to direct electromagnetic radiation from the one or more generators to the feature of interest.

3. The viewing system of claim 2 in which the illumination system comprises one or more controllable electromagnetic radiation guides for directing electromagnetic radiation from the one or more generators.

4. The viewing system of claim 1 in which the one or more controllable electromagnetic radiation guides for directing electromagnetic radiation from the dental mirror to the detector comprise plural receiver elements spaced laterally from one another relative to a target area in front of the receiver elements.

5. The viewing system of claim 4 in which the plural receiver elements are mounted on a frame.

6. The viewing system of claim 5 in which the frame is mounted on one or more of a wall, floor, or ceiling.

7. The viewing system of claim 4 in which the one or more controllable electromagnetic radiation guides for directing electromagnetic radiation from the dental mirror to the detector further comprise one or more intermediate guides connected to direct electromagnetic radiation from one or more of the plural receiver elements to the detector.

8. The viewing system of claim 1 in which the one or more controllable electromagnetic radiation guides for directing electromagnetic radiation from the dental mirror to the detector comprise one or more fiber optic cables.

9. The viewing system of claim 1 in which the one or more controllable electromagnetic radiation guides for directing electromagnetic radiation from the dental mirror to the detector comprise one or more optical elements.

10. The viewing system of claim 1 in which said display comprises a head mounted 3D display.

11. The viewing system of claim 1 in which the display is connected to a second display to co-display the image with a second image, and further comprising a patient selective filter for blocking electromagnetic radiation from the display of the image and a user selective filter for blocking electromagnetic radiation from the display of the second image.

12. The viewing system of claim 11 in which the selective filter comprises one or more active or passive viewers.

13. The viewing system of claim 1 further comprising an eye tracker connected to send control signals to the control system.

14. The viewing system of claim 1 in which the detector comprises two or more detectors.

15. The viewing system of claim 1 in which the control system is configured to continuously loop through the steps to identify, select, and track other features of interest visible in the dental mirror.

16. A viewing method comprising:
    detecting electromagnetic radiation with a detector mounted on a frame;
    guiding the electromagnetic radiation from a target area to the detector using one or more controllable electromagnetic radiation guides mounted on the frame;
    identifying a dental mirror, disposed within a field of view of the detector in use, with a control system connected to receive signals from the detector;
    identifying a feature of interest that is within the field of view and that is visible in the dental mirror with the control system;
        selecting with the control system for detection and tracking by the detector the feature of interest that is visible in the dental mirror by directing electromagnetic radiation to the detector using the dental mirror and the controllable electromagnetic radiation guides; wherein the detection and tracking includes manipulating the controllable electromagnetic radiation guides to view the feature of interest from a different field of view or optimal angle of view;
    tracking the dental mirror with the control system;
    continuing to tracking with the control system the feature of interest, visible in the dental mirror, independently of the dental mirror, the feature of interest being distinct from the dental mirror; and displaying an image of the feature of interest on one or more displays.

17. The viewing method of claim 16 in which identifying the dental mirror further comprising cycling through plural fields of view received by the one or more controllable electromagnetic radiation guides until the dental mirror is identified.

18. The viewing method of claim 16 in which the dental mirror is identifiable within two or more fields of view of plural fields of view received by the one or more controllable electromagnetic radiation guides, and further comprising selecting one or more of the two or more fields of view for display based on predetermined criteria.

19. The viewing method of claim 18 in which the predetermined criteria comprises a desired shape, and selecting one or more of the two or more fields of view further comprises selecting a field of view that includes a shape, of the dental mirror, that most closely corresponds to the desired shape.

20. A viewing system, comprising:
a detector of electromagnetic radiation mounted on a frame;
plural receiver elements mounted on the frame spaced laterally from one another relative to a target area in front of the receiver elements for directing electromagnetic radiation from a dental mirror, disposed within the target area in use, to the detector; and
a control system connected to receive signals from the detector, and configured to:
identify and track the dental mirror;
identify a feature of interest that is within the field of view and that is visible in the dental mirror;
select for detection and tracking by the detector the feature of interest that is visible in the dental mirror by directing electromagnetic radiation to the detector using the dental mirror and the plural receiver elements, and
continue to track the feature of interest independently of the dental mirror, the feature of interest being distinct from the dental mirror;
wherein the detection and tracking includes manipulating the plurality of receiver elements to view feature of interest from a different field of view or optimal angle of view;
displaying an image on a display in which the feature of interest is visible.

* * * * *